(12) United States Patent
Moseley

(10) Patent No.: US 6,173,602 B1
(45) Date of Patent: Jan. 16, 2001

(54) TRANSITION METAL OXIDE GAS SENSOR

(76) Inventor: Patrick T. Moseley, 100 Ellsworth Pl., Chapel Hill, NC (US) 27516

( * ) Notice: Under 35 U.S.C. 154(b), the term of this patent shall be extended for 0 days.

(21) Appl. No.: 09/132,216

(22) Filed: Aug. 11, 1998

(51) Int. Cl.[7] .................................................. G01N 27/12
(52) U.S. Cl. ............................................. 73/31.06; 422/88
(58) Field of Search ............................... 73/31.05, 31.06; 422/83, 88

(56) References Cited

U.S. PATENT DOCUMENTS

| 3,603,954 | 9/1971 | Takeuchi . | |
|---|---|---|---|
| 3,879,985 | 4/1975 | Maslen . | |
| 4,045,729 | 8/1977 | Loh . | |
| 4,111,034 | 9/1978 | Hubner . | |
| 4,443,791 | 4/1984 | Risgin et al. . | |
| 4,453,151 | 6/1984 | Leary et al. . | |
| 4,542,640 | * 9/1985 | Clifford | 73/31.06 |
| 4,587,104 | 5/1986 | Yannopoulos . | |
| 4,731,226 | 3/1988 | Takahata et al. . | |
| 4,916,935 | * 4/1990 | Novack et al. | 73/31.06 |
| 5,082,789 | 1/1992 | Morrison et al. . | |
| 5,342,701 | * 8/1994 | Miremadi et al. | 428/701 |
| 5,389,340 | 2/1995 | Satake . | |

FOREIGN PATENT DOCUMENTS

| 46989 | * 3/1982 | (EP) | 73/31.06 |
|---|---|---|---|
| 63-65354 | * 3/1988 | (JP) | 73/31.06 |
| 63-223552 | * 9/1988 | (JP) | 73/31.06 |
| 2-263146 | * 10/1990 | (JP) | 73/31.06 |
| 3-59450 | * 3/1991 | (JP) | 73/31.06 |

OTHER PUBLICATIONS

Ferroni, Matteo, et al., "Characterization of a Molybdenum Oxide Sputtered Thin Film as a Gas Sensor", This Solid Films, vol. 307, 1997, pp. 148–151.

* cited by examiner

Primary Examiner—Daniel S. Larkin
(74) Attorney, Agent, or Firm—James Creighton Wray; Meera P. Narasimhan

(57) ABSTRACT

A sensor and a sensing method for use in a gas or gaseous mixture is provided. The sensor includes a gas sensitive material, $MO_{3-x}$, in which M is predominantly or exclusively MO and $MO_{3-x}$ is a substoichiometric molybdenum trioxide which exhibits a response in the form of an increase or a decrease in an electrical property of the material in the presence of a gas. The gas sensitive material is in communication with two or more electrodes and is arranged for being contacted with a gas or gaseous mixture. The electrodes are in direct communication with the gas sensitive material by being in contact therewith. The sensor incorporates a temperature sensor. The sensor includes a heating element.

29 Claims, 6 Drawing Sheets

TRANSITION METAL OXIDE GAS SENSOR

BACKGROUND OF THE INVENTION

A large number of semiconductor gas sensors are presently in use in many parts of the world largely to provide early warning of the development of an explosion hazard (e.g. escaping flammable gas) or the presence of toxic gases or vapors in ambient air.

A sensing element normally comprising a semiconducting material and presenting a high surface-to-bulk ratio is deployed on a heated substrate between two metallic electrodes. The presence of gas posing a hazard is detected by a sensible change in the resistance of the semiconducting element by means of the electrodes that are incorporated in a suitable electric circuit. The device is thus a gas-sensitive resistor.

The most commonly used material in gas sensitive resistors used to measure impure gases in air is tin dioxide. Tin dioxide sensors, though often useful in particular alarm functions, have generally been found to suffer from a lack of selectivity.

The reactions that allow the detection of target gases normally involve the oxidation of the target gas at the semiconductor (oxide) surface and a concomitant change in the charge carrier density of the material. Unfortunately, changes in relative humidity also give rise to a sensible change in the conductivity of tin dioxide even though, in this case, no oxidation process is possible. In other words, changes in relative humidity amount to an interference with the detection of gases by tin dioxide even though the mechanisms involved in the two responses are different.

Since the reactions that generate the resistance response take place at the oxide surface, a very small amount of second phase additive may modify the behavior substantially.

SUMMARY OF THE INVENTION

The present invention relates to sensors and more particularly to sensors suitable for use in gases and gaseous mixtures.

In a preferred embodiment, a sensor is provided that is suitable for use in a gas or gaseous mixture. The sensor includes a gas sensitive material (as hereinafter defined) that is capable of exhibiting a response in the form of an increase or a decrease in an electrical property of the material in the presence of a gas and that exhibits a small response to changes in the moisture content of the atmosphere.

In another preferred embodiment, the gas sensitive material is provided with two or more electrodes in communication with the gas sensitive material and the gas sensitive material is arranged so as to be capable of being contacted with a gas or gaseous mixture.

A sensor in accordance with the present invention may be used as a gas sensor in quantitative and/or qualitative determinations with gases or gaseous mixtures. The electrodes may be in direct communication with the gas sensitive material by being in contact therewith.

In this specification, the term "gas" preferably embraces a gas as such and any material that may be present in a gaseous phase, one example of which is a vapor.

The gas sensitive material is a material which responds to a target gas rather than to changes in relative humidity. Also, it will be appreciated that in this specification the term "gas sensitive material" means a preferred material which is gas (including vapor) sensitive in respect of an electrical property of the material.

It will be appreciated that the resistance and/or capacitance, and/or impedance of the gas sensitive material depends upon the gas or gaseous mixture contacting the gas sensitive material. Thus, by measuring the resistance and/or capacitance, and/or impedance of the gas sensitive material, the composition of a gas or gaseous mixture can be sensed.

Since the resistance and/or capacitance, and/or impedance of the gas sensitive material tends also to be temperature dependent, the sensor also preferably includes a temperature sensing means. The sensor may also include a heating means to enable operating temperature to be adjusted and/or contaminants to be burnt off if required.

It is to be understood that the sensitivity of a gas sensitive material may depend upon the composition of the gas sensitive material. Thus, by selection of the composition of the gas sensitive material its response to a particular gas may be optimized and its response to interferents, such as changes in relative humidity may be minimized.

The resistance and/or conductance, and/or impedance may be measured directly. Alternatively, the measurement may be carried out indirectly by incorporating the sensor in a feedback circuit of an oscillator such that the oscillator frequency varies with composition of the gas or gaseous mixture. Gas composition may then be determined using an electronic counter. The signal thus produced may be used to modulate a radio signal and thereby be transmitted over a distance (e.g. by telemetry or as a pulse train along an optical fibre).

Examples of gases which have shown responses using a sensor in accordance with the present invention are $H_2$, $C_2H_4$, $NH_3$, $C_3H_8$, $H_2S$, $CH_4$, and $CO$.

In one preferred embodiment of the present invention, the gas sensitive material (as herein defined), has two or more electrodes in communication with said gas sensitive material, and the gas sensitive material and the electrodes are in contact with the same gas.

Preferably, the gas sensitive material has porosity to give a satisfactory surface area for contact with the gas or gaseous mixture when in use.

The gas sensitive material, for example, may be prepared from an oxide or from an appropriate precursor. The oxide or precursor may optionally be prepared by a gel process, such as a sol-gel process or a gel precipitation process.

The powder may be dried and calcined (e.g. for approximately sixteen hours) at a temperature in the range of about 700–1000° C. depending upon the particular composition of gas sensitive material being prepared. The product resulting from calcination, which may be in the form of a cake, may be ground as required to give a fine powder. If required, grinding and calcination may be repeated several times in order to obtain a more suitable powder.

Subsequently, the fine powder may be pressed (e. g. with the optional addition of a binder, such as a solution of starch or polyvinyl alcohol) into any suitable shape (e. g. a pellet).

The pressing may be followed by a firing (e. g. at the same temperature as the calcination step(s) described above, or at a somewhat higher temperature, for approximately sixteen hours).

In addition to assisting in the binding of the powder into desired shapes, the binder also burns out during the firing stage giving rise to porosity.

As an alternative, a powder for subsequent calcination may be prepared, for example, by spray drying a solution (e.g. an aqueous solution) of appropriate starting material (e.g. a metal oxalate, metal acetate, or metal nitrate).

Electrodes may be applied to the prepared gas sensitive material in any suitable manner. For example, electrodes (e.g. gold electrodes) may be applied by means of screen printing or sputtering.

Alternatively to preparing a sensor by forming a pellet and applying electrodes as disclosed above, a sensor in accordance with the present invention may be formed in any suitable manner. Thus, for example, a parallel plate configuration may be fabricated by applying a first electrode (e.g. of gold) to an insulating substrate (e.g. by screen printing or sputtering), forming a gas sensitive material layer covering at least a portion of the first electrode (e.g. by deposition, for example by screen printing or doctor blading from a suspension or a colloidal dispersion and firing at a temperature in range of about 450–950° C. to promote adhesion and mechanical integrity) and forming a second electrode (e.g. of gold) on the gas sensitive material layer (e.g. by screen printing or sputtering).

The second electrode is preferably permeable to facilitate access of gas or gaseous mixture in which the sensor is to be used to the gas sensitive material layer.

By way of further example, a coplanar configuration may be used in the preparation of a sensor in accordance with the present invention.

In such a coplanar configuration, interdigitated electrodes (e.g. of gold) may be formed on an insulating substrate (e.g. by screen printing or by sputtering or by photolithography and etching). The interdigitated electrodes are subsequently covered with a gas sensitive material layer (e.g. by means of deposition, for example by screen printing or doctor blading, from a suspension or a colloidal dispersion) and firing at a temperature in the range of about 450–950° C. to promote adhesion and mechanical integrity.

The gas sensitive material disclosed by the present invention is comprised of a metal oxide of general formula $MO_{3-x}$, in which formula M is predominantly or exclusively molybdenum. The oxide is thus derived from molybdenum trioxide, $MoO_3$, either by reduction so that in the formula $MO_{3-x}$ the value of x is invested with a finite value up to around 0.3, by a thermal treatment, or by substituting a small fraction of the molybdenum by a metal with a principal valence of less than six in order to stabilize the structure of the substoichiometric phase, $MO_{3-x}$.

In one example, the substoichiometric phase, $MO_{3-x}$, may be stabilized by the incorporation of 7% of tantalum, which results in an overall stoichiometry Of $MO_{2.8}$. Any one of a number of transition metal ions with stable valence of less than 6 could stabilize the required structure in accordance with the spirit of the present invention, provided that the substituent transition metal ion has a radius of a suitable size to match the structure.

These and further and other objects and features of the invention are apparent in the disclosure, which includes the above and ongoing written specification, with the claims and the drawings.

DETAILED DESCRIPTION OF THE PREFERRED EMBODIMENTS

Figure 1:
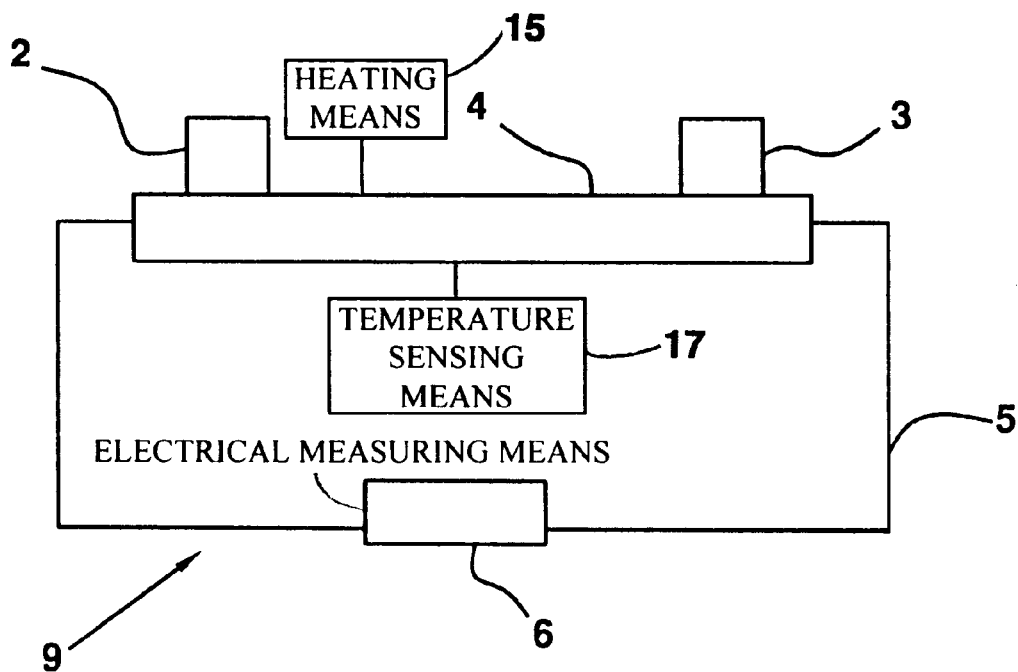
FIG. 1 is a diagrammatic representation of one form of a sensor in accordance with the present invention.

Referring now to FIG. 1 of the drawings, there is shown a sensor 9 comprising a gas sensitive material 4 and, in contact with the gas sensitive material, gold electrodes 2 and 3. The gas sensitive material may be carried by a substrate (e.g. of alumina) (not shown).

Conductors 5 are provided to connect the electrodes 2 and 3 respectively to electrical measuring means 6 for measuring the resistance and/or capacitance, and/or impedance of the gas sensitive material 4.

In operations gas or gaseous mixture is contacted with the gas sensitive material 4.

The resistance and/or conductance, and/or impedance is measured by the electrical measuring means 6. Changes in the composition of the gas or gaseous mixture which result in a change of resistance and/or conductance, and/or capacitance, and/or impedance are observed as changes in the resistance and/or conductance, and/or capacitance and/or impedance recorded by the measuring means 6. Sensor 9 may include temperature sensing means 17 for sensing temperature and heating means 15 for heating the sensor.

Figure 2:
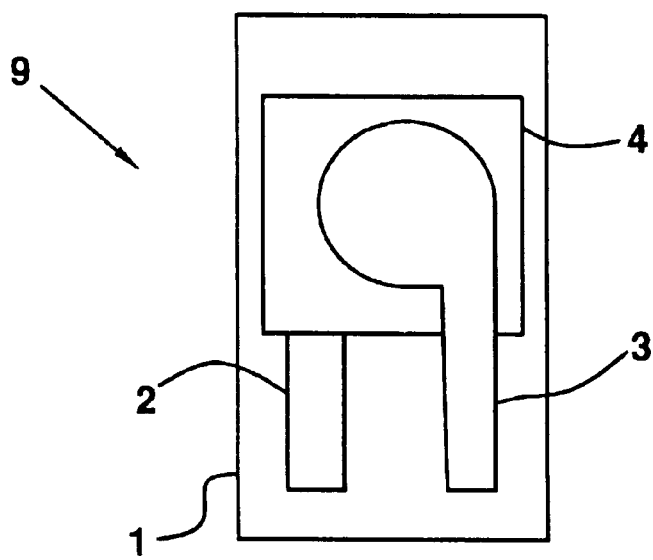
FIGS. 2 and 3 represent diagrammatically a parallel plate sensor in accordance with the present invention and a partially completed parallel plate sensor respectively.

Referring now to FIG. 2, there is shown (in plan view) an insulating substrate 1 (e.g. an alumina ceramic tile) upon which is formed a first electrode 2 (e.g. of gold), a gas sensitive material layer 4 comprising a gas sensitive material in accordance with the present invention and a second electrode 3 (e.g. of gold).

A parallel plate sensor 9, as shown in FIG. 2, may be fabricated by applying the first electrode 2 (e.g. of gold) to the insulating substrate 1 (e.g. by screen printing or sputtering), forming a gas sensitive material layer 4 by deposition, for example by screen printing or doctor blading, from a suspension or a colloidal dispersion and firing at a temperature in the range 450–950° C. to promote adhesion and mechanical integrity and forming a second electrode 3 (e.g. of gold) on the gas sensitive material layer 4, (e.g. by screen printing or sputtering).

Figure 3:
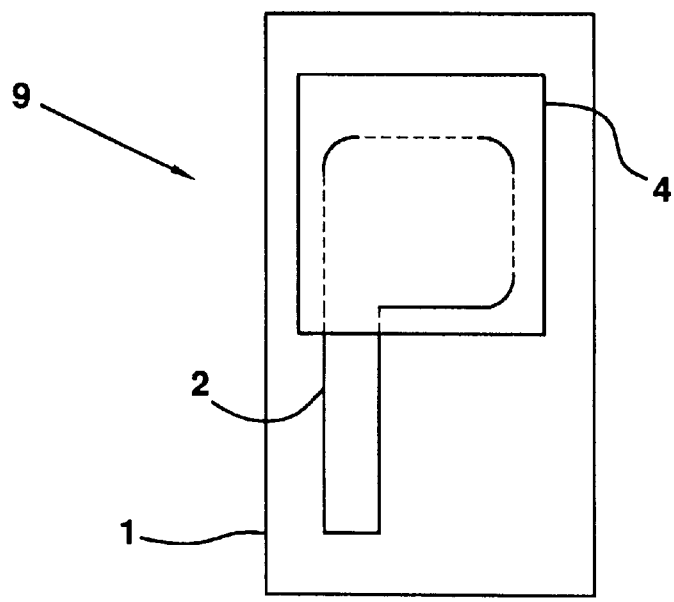

In order to facilitate understanding of the construction of the sensor of FIG. 2, reference may be made to FIG. 3, which shows a parallel plate sensor 9 of the type shown in FIG. 2 partially completed inasmuch as the second electrode 3 has not been formed. FIG. 3 thus shows the insulating substrate 1, the first electrode 2, and the gas sensitive material layer 4 and it is seen that the portion of the first electrode 2 covered by the gas sensitive material layer 4 may preferably extend in area to substantially the same extent as the second electrode 3.

In operation, the first electrode 2 and second electrode 3 are connected to an electrical measuring means (not shown) for measuring the resistance and/or capacitance, and/or impedance of the gas sensitive material layer 4 and the sensor is contacted with a gas or gaseous mixture. The resistance and/or capacitance, and/or impedance is measured by the electrical measuring means and changes in the composition of the gas or gaseous mixture which result in a change of resistance and/or capacitance, and/or impedance are observed as changes in the resistance and/or capacitance, and/or impedance recorded by the electrical measuring means.

Figure 4:
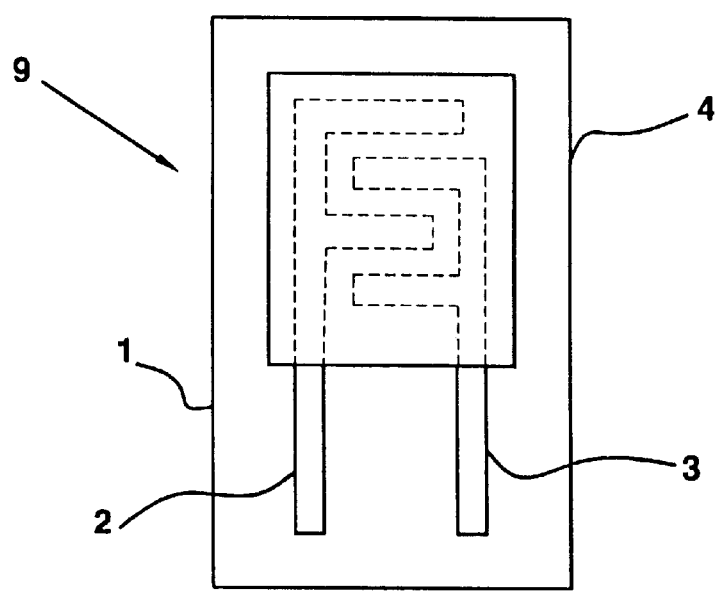
FIG. 4 is a diagrammatic representation of a coplanar sensor in accordance with the present invention.

Referring now to FIG. 4, there is shown (plan view) an insulating substrate 1 (e.g. an alumina ceramic tile upon which are formed electrodes 2 and 3 (e.g. both of gold), and a gas sensitive material layer 4 comprising a gas sensitive material in accordance with the present invention. It is seen from the lines shown in dotted form in FIG. 4 that the portions of the first electrode 2 and second electrode 3 covered by the gas sensitive material layer 4 are interdigitated.

The first electrode 2 and the second electrode 3 may be provided on the insulating substrate 1 by any suitable method. For example, the methods disclosed for providing electrodes 2 and 3 in the parallel plate sensor described hereinbefore with reference to FIG. 2 and FIG. 3 may be used.

The gas sensitive material layer 4 shown in FIG. 4 may be prepared by any suitable method. For example, the methods disclosed for preparing gas sensitive material layer 4 in FIG. 2 and FIG. 3 may be used.

Figure 5:
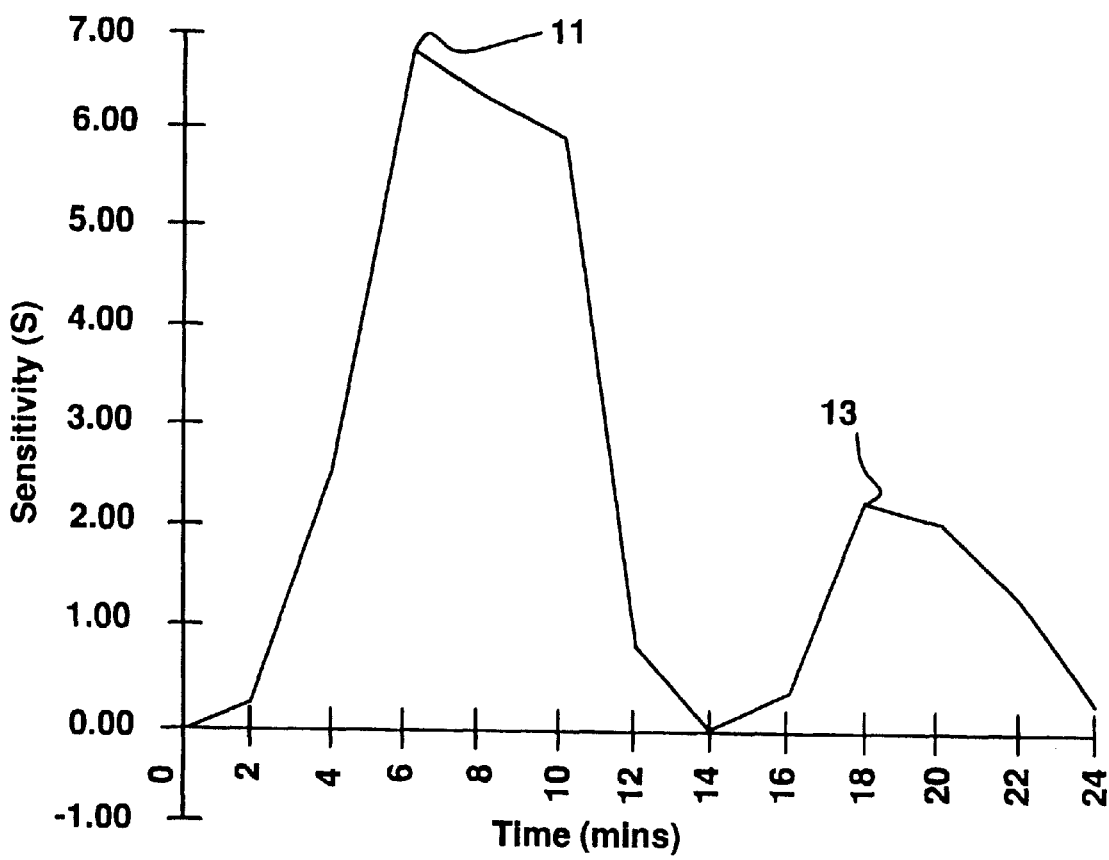
FIG. 5 is the response, in terms of sensitivity ($(G-G_0)/G_0$), where G is conductance in gas and $G_0$ is conductance in air, and time, of a sensor of $MO_{3-x}$. The $MO_{3-x}$ here was manufactured by heating $MoO_3$ above its melting point, to 1000° C., in an alumina crucible for sixteen hours and regrinding the dark blue/purple material thus obtained. The sensor took the form of a cylindrical porous pellet, approximately two mm thick and one cm in diameter, with gold electrodes and was heated by an external tube furnace arranged coaxially with the pellet and with the gas concentrations indicated in a background atmosphere of air at about 500° C.

FIG. 5 is the response, in terms of sensitivity and time, of a sensor of $MO_{3-x}$. The $MO_{3-x}$ here was manufactured by heating $MoO_3$ above its melting point, to 1000° C., in an alumina crucible for sixteen hours and regrinding the dark blue/purple material thus obtained. The sensor took the form of a cylindrical porous pellet, approximately two mm thick and one cm in diameter, with gold electrodes and was heated by an external tube furnace arranged coaxially with the pellet and with the gas concentrations indicated in a background atmosphere of air at 500° C.

Gases that the sensor may detect include, but are not limited to, hydrogen, ethene, ammonia, ozone, propane, methane, carbon monoxide, chlorine, nitrogen dioxide, sulphur dioxide, or hydrogen sulphide.

FIG. 5 shows the gas response of a $MO_{3-x}$ sensor in air. The first peak 11 is the response to 1% of carbon monoxide. The second peak 13 is the response to 1% of methane. The y-axis shows the sensitivity of the sensor, which is a function of the conductance in clean air, Go, and the conductance in (air plus the gas to be detected), G, as follows:

$$S=(G-Go)/Go$$

The value of the sensitivity changes as the composition of the atmosphere is altered at times indicated on the x axis.

The graph shows that at the start (time zero) the sensor is in air so that the sensitivity is zero. As soon as the first gas (carbon dioxide) is introduced (at a concentration of 1% in air), right after time zero, the sensitivity rises to reach a peak at a value near 7.0. As soon as the atmosphere is returned to pure air (at around ten minutes on the x-axis), the sensitivity begins to drop to reach zero once more (at fourteen minutes). The second gas, methane, is then introduced, also at a concentration of 1%, so that the sensitivity rises once more to a new peak at around 2.2.

Figure 6:
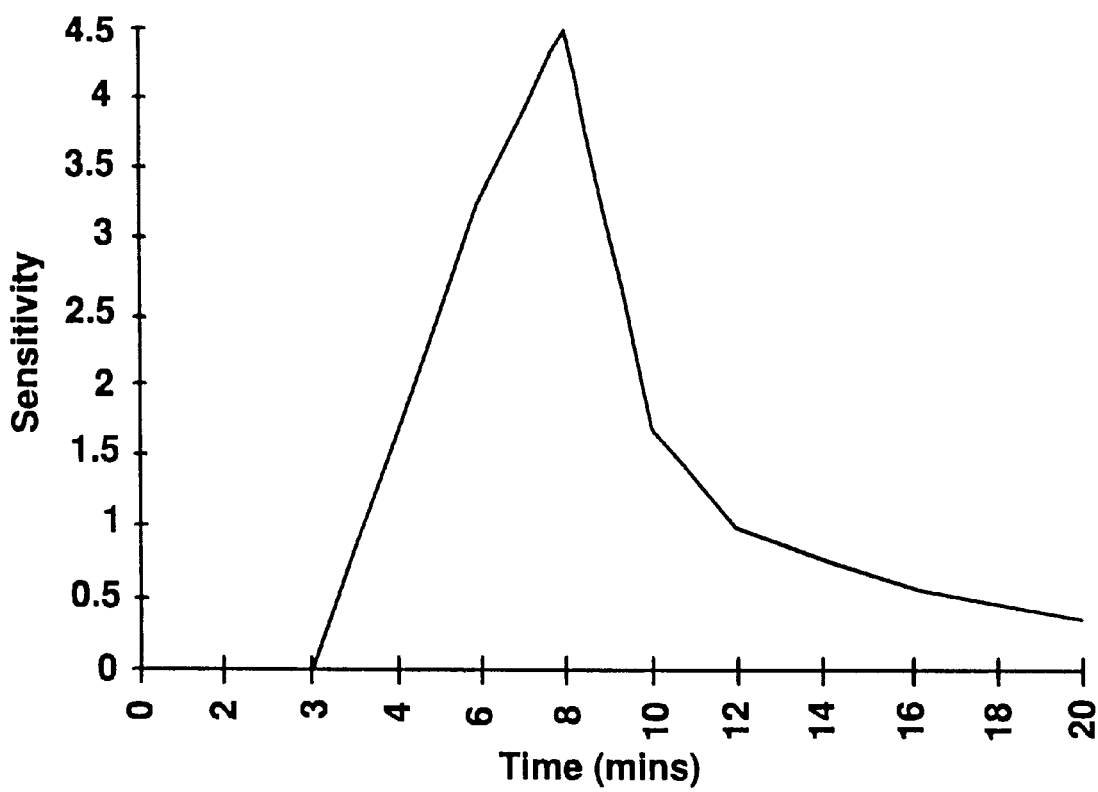
FIG. 6 is a graph of the response in terms of sensitivity of a $MO_{3-x}$ sensor in air to fifty ppm hydrogen sulphide.
Figure 7:
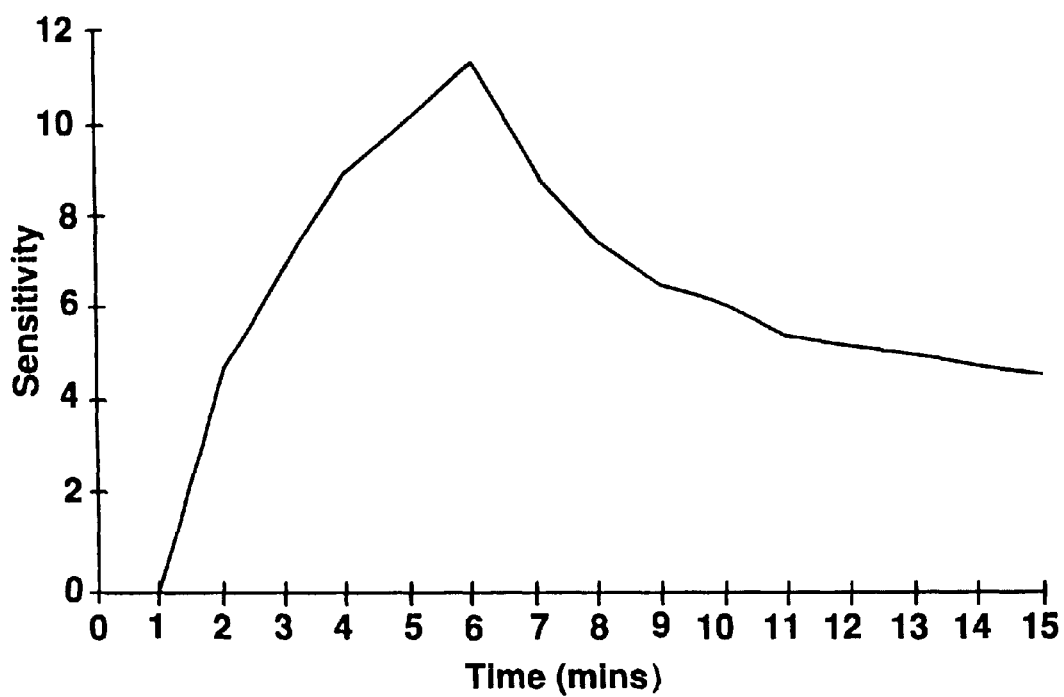
FIG. 7 is a graph of the response in terms of sensitivity of a $MO_{3-x}$ sensor in air to 500 ppm ammonia.
Figure 8:
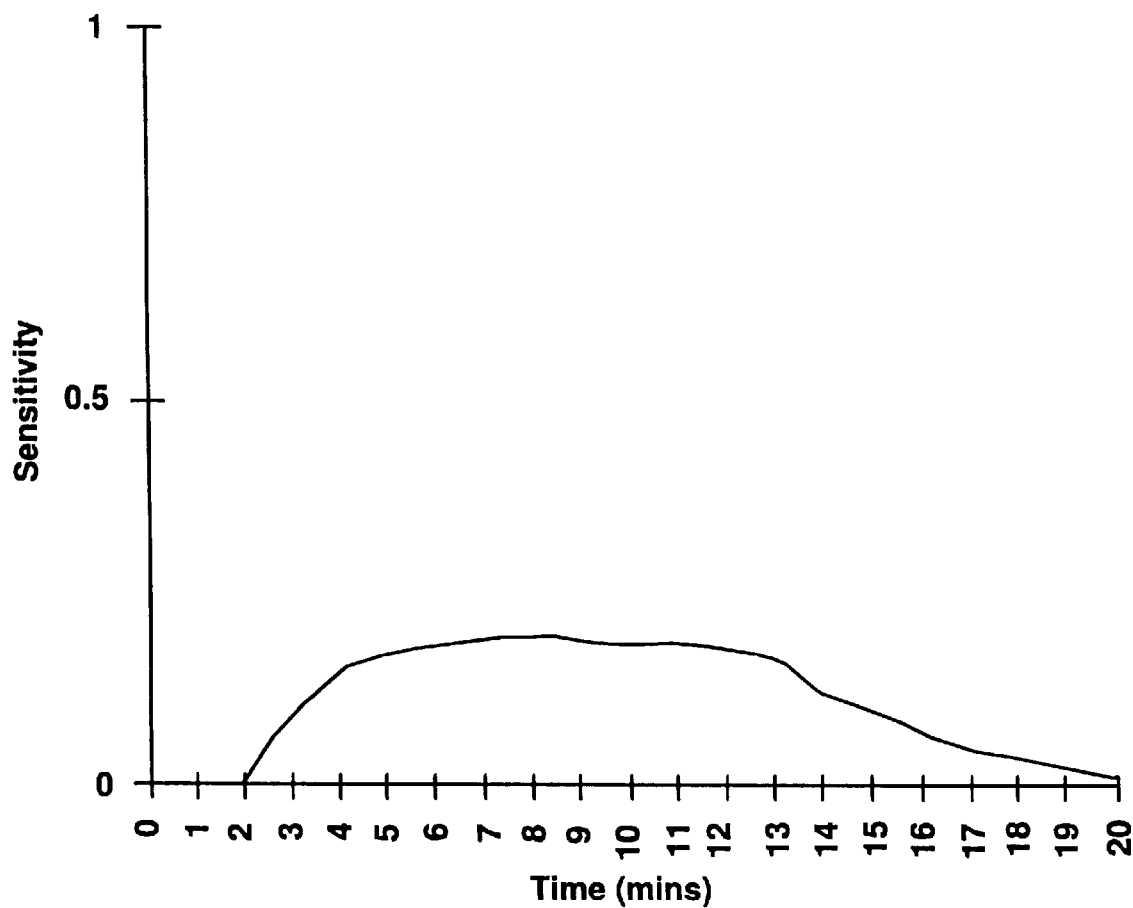
FIG. 8 is a graph of the response in terms of sensitivity of a $MO_{3-x}$ sensor in dry air to a ten minute pulse of wet air.

FIGS. 6, 7, and 8 are the responses of a thick film sensor of $MoO_{0.93}Ta_{0.07}O_{2.8}$ to $H_2S$, to $NH_3$, and to moisture, respectively. The $MO_{3-x}$ was a thick film of $Mo_{0.93}Ta_{0.07}O_{2.8}$ manufactured by firing together the constituent oxides at 800° C. The response is given in terms of sensitivity, which is defined as $(G-G_0)/G_0$, where G is the conductance in gas and $G_0$ is the conductance in air.

FIG. 6 is a graph of the gas response in terms of sensitivity of a $MO_{3-x}$ sensor at 250° C. in air to a five minute pulse of fifty parts per million of hydrogen sulfide. The graph shows that when hydrogen sulfide is introduced (at three minutes) the sensitivity starts rising and reaches a peak. When the atmosphere is returned to air the sensitivity drops (eight minutes).

FIG. 7 is a graph of the gas response in terms of sensitivity of a $MO_{3-x}$ sensor at 250° C. in air to a five minute pulse of 500 parts per million of ammonia. The graph shows that when ammonia is introduced (at one minute) the sensitivity starts rising and reaches a peak. When the atmosphere is returned to air the sensitivity drops (six minutes).

FIG. 8 is a graph of the gas response in terms of sensitivity of a $MO_{3-x}$ sensor at 250° C. in dry air to a ten minute pulse of wet air (passed through a bubbler of water at room temperature). The graph shows the sensitivity of the sensor to the saturation of an atmosphere of air (two minutes) and ending with water vapor (twelve minutes).

While the invention has been described with reference to specific embodiments, modifications and variations of the invention may be constructed without departing from the scope of the invention, which is defined in the following claims.

I claim:

1. A sensor for detecting gases comprising plural electrodes, a gas sensitive material in contact with each electrode, the gas sensitive material being $MO_{3-x}$, wherein M is predominantly or exclusively Mo and $MO_{3-x}$ is a substoichiometric molybdenum trioxide which includes five-valent transitional metal ions and which exhibits a response in the form of an increase or a decrease in an electrical property of the material in the presence of a gas or gaseous mixture.

2. The sensor as claimed in claim 1, wherein the plural electrodes consist of at least two electrodes in communication with the gas sensitive material and wherein said gas sensitive material and the electrodes are arranged so as to be capable of being contacted with a gas or gaseous mixture.

3. The sensor as claimed in claim 2, wherein the electrodes are in direct communication with the gas sensitive material by being in contact therewith.

4. The sensor as claimed in claim 1, wherein the sensor incorporates a temperature sensing means.

5. The sensor as claimed in claim 1, wherein the sensor includes a heating means.

6. A method for effecting determination in a gas or gaseous mixture which comprises providing a gas sensor with plural electrodes, each electrode in contact with a gas sensitive material having a formula $MO_{3-x}$ in which M is predominantly or exclusively Mo and $MO_{3-x}$ is a substoichiometric molybdenum trioxide which includes five-valent transitional metal ions, contacting the sensor with the gas or gaseous mixture and measuring the electrical response of the sensor, contacting each electrode and the gas sensitive material with a gas or gaseous mixture wherein the gas sensitive material as herein before defined exhibiting a response in the form of an increase or a decrease in an electrical property of the material in the presence of the gas or gaseous mixture, detecting the change in the electrical property by the electrodes, measuring the change in electrical property and determining the gas concentration.

7. The method as claimed in claim 6, the plural electrodes further comprising at least two electrodes in communication with the gas sensitive material, and contacting the gas sensitive material and the electrodes with the same gas or gaseous mixture.

8. The method as claimed in claim 6, further comprising providing the gas sensitive material with a porosity and increasing surface area for contact with the gas or gaseous mixture.

9. The method as claimed in claim 6, wherein the measuring further comprises measuring the resistance of the sensor.

10. The method as claimed in claim 6, wherein the measuring further comprises measuring the capacitance of the sensor.

11. The method as claimed claim 6, wherein the measuring further comprises measuring the impedance of the sensor.

12. The method as claimed in claim 6, further comprising detecting hydrogen, ethene, ammonia, propane, methane, carbon monoxide, ozone, chlorine, nitrogen dioxide, sulphur dioxide, or hydrogen sulphide with the sensor.

13. A sensor for detecting gases comprising plural electrodes having first and second portions, a gas sensitive material in contact with portions of each electrode, and a gas or gaseous mixture for contacting the gas sensitive material, wherein the gas sensitive material is $MO_{3-x}$, wherein M is predominantly or exclusively Mo and $MO_{3-x}$ is a substoichiometric molybdenum trioxide exhibiting a change in an electrical property in the presence of the gas or gaseous mixture, wherein a small fraction of the Mo is substituted with metal having a principal valence not greater than six, and wherein the value of x in the gas sensitive material $MO_{3-x}$ is not greater than 0.3.

14. The sensor of claim 13, wherein the electrodes directly contact the gas sensitive material in said one portions.

15. The sensor of claim 13, further comprising a temperature sensor for sensing a temperature.

16. The sensor of claim 13, further comprising a heater connected to the sensor for heating.

17. A sensor for detecting gases comprising plural electrodes having first and second portions, a gas sensitive material in contact with portions of each electrode, and a gas or gaseous mixture for contacting the gas sensitive material, wherein the gas sensitive material is $MO_{3-x}$, wherein M is predominantly or exclusively Mo and $MO_{3-x}$ is a substoichiometric molybdenum trioxide exhibiting a change in an electrical property in the presence of the gas or gaseous mixture, further comprising metal ions in the gas sensitive material $MO_{3-x}$ having a valence not greater than six and the value of x is greater than zero.

18. The sensor of claim 17, wherein the metal ions are transition metal ions.

19. The sensor of claim 18, wherein the transition metal is tantalum.

20. A method for sensing gases comprising providing a gas sensor with plural electrodes, partially covering each electrode with a gas sensitive material, contacting each electrode and the gas sensitive material with a gas or gaseous mixture, changing an electrical property of the gas sensitive material in response to the gas or gaseous mixture, detecting the change as an increase or a decrease in the electrical property of the material in the presence of the gas or gaseous mixture by the electrodes, measuring the change in the electrical property and determining the gas concentration, wherein the gas sensitive material has a formula $MO_{3-x}$ in which M is predominantly or exclusively Mo and $MO_{3-x}$ is a substoichiometric molybdenum trioxide, wherein a small fraction of the Mo is substituted with metal having a principal valence not greater than six, and wherein the x in the gas sensitive material $MO_{3-x}$ has a value not greater than 0.3.

21. The method of claim 20, further comprising providing the gas sensitive material with a porous and increased surface area for contacting with the gas or gaseous mixture.

22. The method of claim 20, wherein the measuring further comprises measuring the resistance of the sensor.

23. The method of claim 20, wherein the measuring further comprises measuring the capacitance of the sensor.

24. The method of claim 20, wherein the measuring further comprises measuring the impedance of the sensor.

25. The method of claim 20, wherein the detecting comprises detecting hydrogen, ethene, ammonia, propane, methane, carbon monoxide, or hydrogen sulphide with the sensor.

26. A method for sensing gases comprising providing a gas sensor with Plural electrodes, partially covering each electrode with a gas sensitive material, contacting each electrode and the gas sensitive material with a gas or gaseous mixture, changing an electrical property of the gas sensitive material in response to the gas or gaseous mixture, detecting the change as an increase or a decrease in the electrical property of the material the presence of the gas or gaseous mixture by the electrodes, measuring the change in the electrical property and determining the gas concentration, wherein the gas sensitive material has a formula $MO_{3-x}$ in which M is predominantly or exclusively Mo and $MO_{3-x}$ is a substoichiometric molybdenum trioxide, wherein a small fraction of the Mo is substituted with metal having a principal valence not greater than six and the value of x is greater than zero.

27. A gas sensor comprising plural electrodes having first and second portions, a gas sensitive material covering one portion of each electrode, wherein the gas sensitive material is responsive to gas and not to changes in relative humidity, and a gas or gaseous mixture for contacting the electrodes and the gas sensitive material, wherein the gas sensitive material is $MO_{3-x}$, wherein M is predominantly or exclusively Mo and $MO_{3-x}$ is a substoichiometric molybdenum trioxide exhibiting a change in an electrical property in the presence of the gas or gaseous mixture, wherein a small fraction of the Mo is substituted with metal having a principal valence not greater than six, and wherein the value of x in the gas sensitive material $MO_{3-x}$ is not greater than 0.3.

28. A gas sensor comprising plural electrodes having first and second portions, a gas sensitive material covering one portion of each electrode, wherein the gas sensitive material is responsive to gas and not to changes in relative humidity, and a gas or gaseous mixture for contacting the electrodes and the gas sensitive material, wherein the gas sensitive material is $MO_{3-x}$, wherein M is predominantly or exclusively Mo and $MO_{3-x}$ is a substoichiometric molybdenum trioxide exhibiting a change in an electrical property in the presence of the gas or gaseous mixture, further comprising metal ions in the gas sensitive material $MO_{3-x}$ having a valence not greater than six and the value of x is greater than zero.

29. The sensor of claim 28, wherein the metal ions are of transition metal ions.

* * * * *

UNITED STATES PATENT AND TRADEMARK OFFICE
CERTIFICATE OF CORRECTION

PATENT NO. : 6,173,602 B1
APPLICATION NO. : 09/132216
DATED : January 16, 2001
INVENTOR(S) : Patrick T. Moseley It is certified that error appears in the above-identified patent and that said Letters Patent is hereby corrected as shown below:

Column 5, line 60, change "dioxide" to --monoxide--.

Signed and Sealed this

Fourth Day of August, 2009

JOHN DOLL
*Acting Director of the United States Patent and Trademark Office*